United States Patent
Santandrea et al.

(10) Patent No.: US 10,927,122 B2
(45) Date of Patent: Feb. 23, 2021

(54) SYNTHESIS OF NOROXYMORPHONE

(71) Applicant: SIEGFRIED AG, Zofingen (CH)

(72) Inventors: Ernesto Santandrea, Zürich (CH); Beat Theodor Weber, Zofingen (CH); Andreas Boudier, Zürich (CH); Oliver Geiseler, Basel (CH); Patrick Jeger, Pratteln (CH)

(73) Assignee: SIEGFRIED AG, Zofingen (CH)

( * ) Notice: Subject to any disclaimer, the term of this patent is extended or adjusted under 35 U.S.C. 154(b) by 0 days.

(21) Appl. No.: 16/769,099

(22) PCT Filed: Nov. 29, 2018

(86) PCT No.: PCT/EP2018/082986
§ 371 (c)(1),
(2) Date: Jun. 2, 2020

(87) PCT Pub. No.: WO2019/110413
PCT Pub. Date: Jun. 13, 2019

(65) Prior Publication Data
US 2020/0385397 A1    Dec. 10, 2020

(30) Foreign Application Priority Data

Dec. 5, 2017 (EP) .................................... 17205507

(51) Int. Cl.
*C07D 491/08* (2006.01)

(52) U.S. Cl.
CPC ................................ *C07D 491/08* (2013.01)

(58) Field of Classification Search
CPC .................................................... C07D 491/08
See application file for complete search history.

(56) References Cited

FOREIGN PATENT DOCUMENTS

| WO | 2008130553 A1 | 10/2008 |
|----|---------------|---------|
| WO | 2015015147 A1 | 2/2015  |
| WO | 2015107472 A1 | 7/2015  |
| WO | 2016005923 A1 | 1/2016  |

OTHER PUBLICATIONS

International Search Report and Written Opinion dated Jan. 30, 2019 for corresponding PCT Application No. PCT/EP2018/082986.

*Primary Examiner* — Patricia L Morris
(74) *Attorney, Agent, or Firm* — Polsinelli PC

(57) ABSTRACT

The present invention relates to the improved synthesis of noroxymorphone of formula (III). Particularly, the invention shows a way how to reduce the impurity level in the product avoiding lengthy purification steps.

5 Claims, 2 Drawing Sheets

Annex (Sample Chromatograms)

Blank

Test sample

Test sample zoomed

Peak-Identity- / SST-solution

SYNTHESIS OF NOROXYMORPHONE

CROSS-REFERENCE TO RELATED APPLICATIONS

Figure 1:
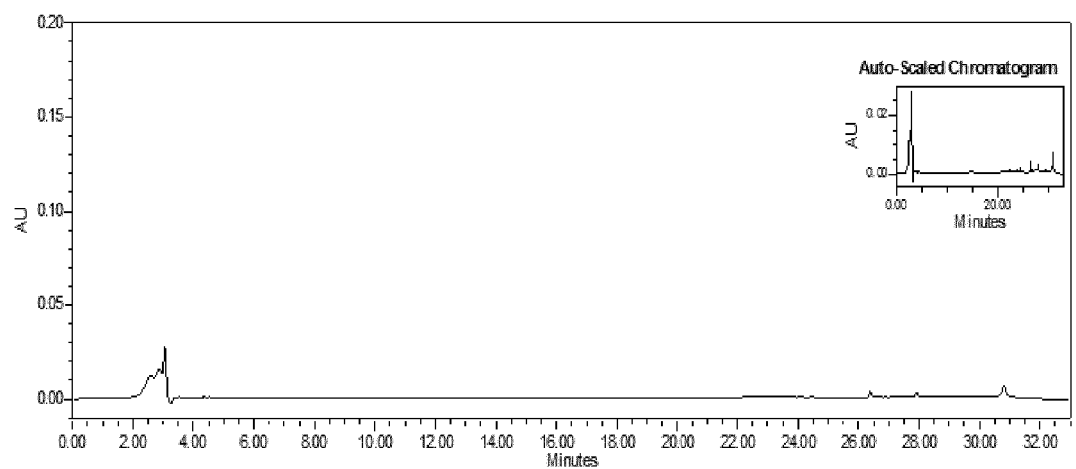

This application is a national stage application (under 35 U.S.C. § 371) of PCT/EP2018/082986, filed Nov. 29, 2018, which claims benefit of European Application No. 17205507.1, filed Dec. 5, 2017, which are incorporated herein by reference in their entireties.

FIELD

The present invention relates to the improved synthesis of noroxymorphone of formula (IIIa).

(IIIa)

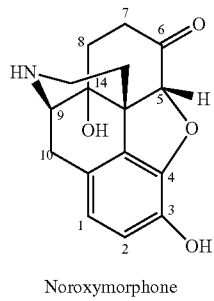

Noroxymorphone

Scheme 1

Particularly, the invention shows a way how to reduce the impurity level in the product avoiding lengthy purification steps.

TECHNICAL BACKGROUND

Noroxymorphone is an intermediate for a variety of pharmaceutical compounds. Scheme 2 shows some examples. However, the noroxymorphone of this invention may be used for all other possible derivatives.

Scheme 2

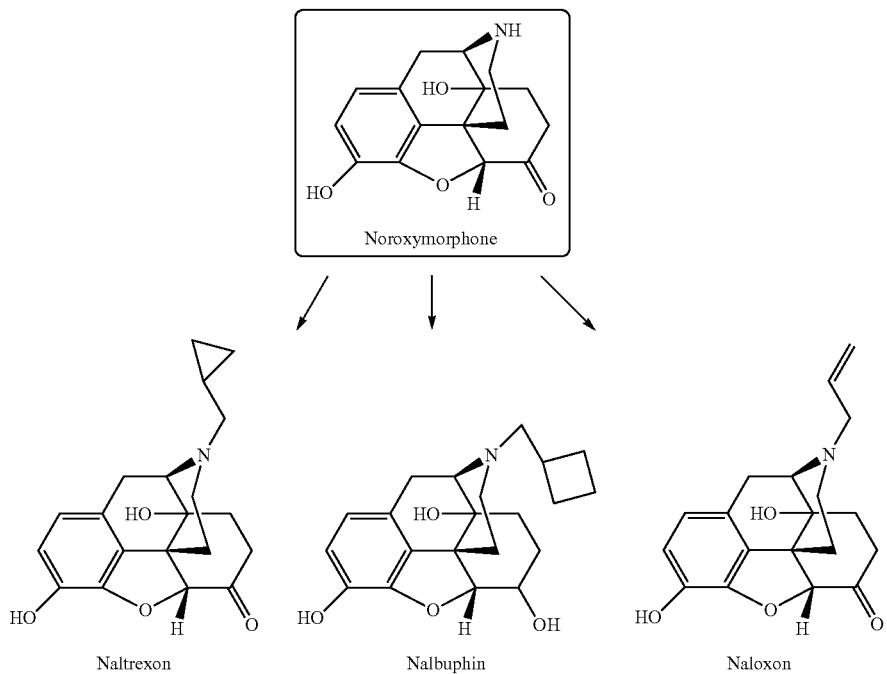

Scheme 2

An efficient way to produce this intermediate is therefore highly valuable for the synthesis of all of these pharmaceutically active compounds.

Noroxymorphone is usually manufactured by a three step synthesis as depicted in scheme 3.

Scheme 3

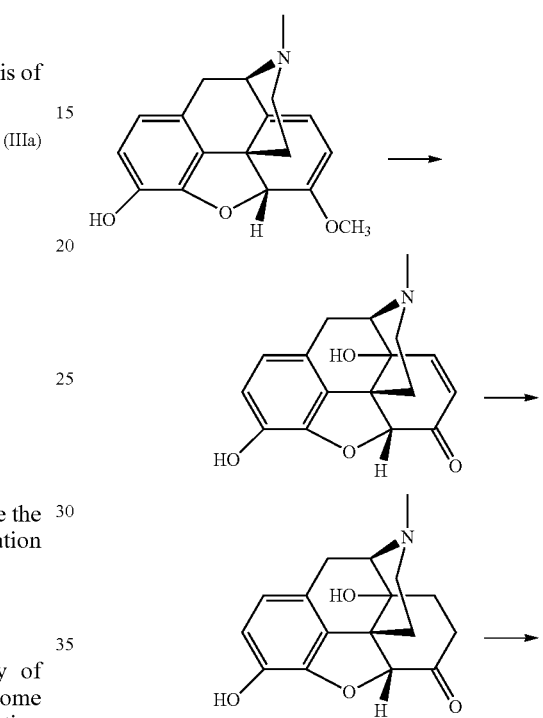

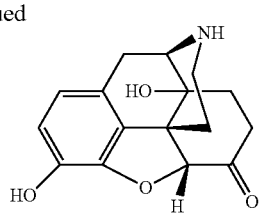

Scheme 3

As already described in WO2016005923 it is known that especially one impurity is to be avoided in the synthesis of noroxymorphone. ABUK-impurities (alpha-beta unsaturated ketone impurities) as shown in scheme 4 are formed during the synthesis of noroxymorphone and are transferred to the final product where they cause severe problems due to their anticipated cancerogenic properties.

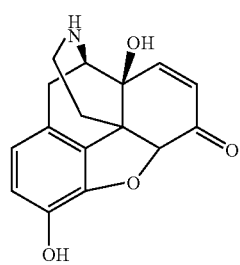

7,8-Didehydronoroxymorphone
(ABUK impurity)

Scheme 4

Noroxymorphone may contain the alpha-beta unsaturated ketone (ABUK) 7,8-didehydronoroxymorphone (Scheme 4), which is the precursor of the analogue N-alkylated ABUK impurity in all subsequent derivatives of noroxymorphone (e.g. naloxone, naltrexone, methylnaltrexone). These impurities are commonly regarded as potentially genotoxic, due to the Michael acceptor moiety in the molecule, and are therefore specified in the low ppm range. The lack of a suitable purification method by crystallization, at any stage of the synthesis, including in the subsequent API synthesis and isolation steps, renders a control strategy for the impurity prior to the API isolation mandatory.

Also known from WO2016005923 is the equilibrium between the ABUK-impurity and the 8-hydroxy-compound in the presence of water.

Scheme 5

Scheme 5 shows that not only the ABUK-impurity, but also the 8-OHN-impurity needs to be reduced during synthesis. Otherwise, the 8-OHN-impurity will react to the ABUK-impurity during workup or storage. Or the ABUK-impurity may be formed as a degradation product from the 8-OHN Impurity in final pharmaceutical formulations.

The problem with ABUK-impurities and the regulatory need of low impurity levels is also described in WO2016005923.

WO2016005923 proposes hydrogenation of the mixture of noroxymorphone and its derivatives with the undesired ABUK-impurity in order to get to a purified product. Unfortunately it also shows that to some extent, the 8-OHN impurity is formed during the process when using an inappropriate acid during hydrogenation, maybe as a result of the hydrolysis of the ABUK-compound. In these cases, the 8-OHN content in the product is higher than before the reaction and raises to up to 1088 ppm. (see p. 132, Table 17 of WO2016005923)

WO2015015147 already describes this phenomenon as "ABUK-regrowth".

WO2015015147 proposes to use an acidic aqueous solution at temperatures greater than 30° C. and lower than 100° C. using different acids. It is further described that in order to prevent reduction of the carbonyl function of noroxymorphone under formation of a morphinone-derivative a two-step synthesis is recommended including a reduction at temperatures below 30° C. However, WO2015015147 does not show the 8-OHN-contents and there is no comprehensive comparative study of the ABUK-regrowth tendency of the products. It seems that also according to WO2015015147 the products with no ABUK gain 50-150 ppm ABUK after stress conditions.

Hence, a suitable way of the reduction of both impurities, the ABUK impurity and also the 8-OHN-Impurity in noroxymorphone compounds and its derivatives is still needed.

SUMMARY OF THE INVENTION

It was now surprisingly observed that by a particular modification of the reaction conditions, particularly the use of sulfuric acid and high temperatures during hydrogenation, the concentration not only of the ABUK-impurity but also of the 8-OHN-impurity could be reduced in a one step process.

Scheme 5

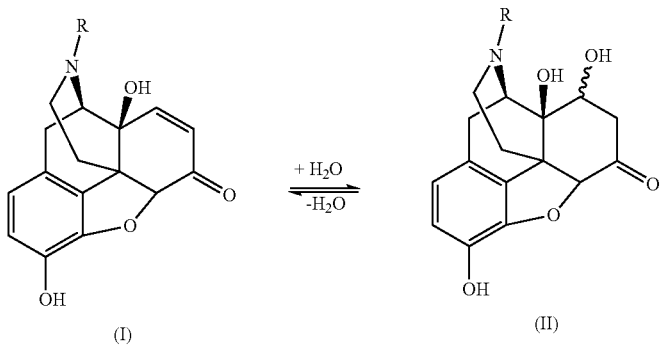

R = Me, 7,8-Didehyrdooxymorphone
R = H, 7,8-Didehydronoroxymorphone
(ABUK)

R = Me, 8-Hyrdoxyoxymorphone
R = H, 8-Hydroxynoroxymorphone
(8-OHN)

DESCRIPTION OF THE INVENTION

As described above, the problem to be solved was to reduce the amount of impurities, especially the ABUK- and the 8OHN-impurities by hydrogenation of the mixture containing noroxymorphone and these impurities.

In a first try, it was believed that higher temperature and/or higher pressure at the hydrogenation of the ABUK-impurity containing mixture could solve the problem. Unfortunately, the prolonged hydrogenation provoked the formation of a new process impurity, identified as noroxymorphol (Scheme 6), and deriving from the reduction of the carbonyl group in noroxymorphone. This impurity is not specified, and exceeds the specification for greatest unknown impurity (≤0.3%).

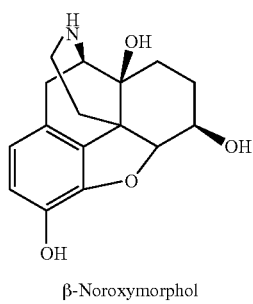 [SMILES: Oc1ccc2c3c1OC1[C@H](O)CC[C@@]4(O)[C@@H](C2)NCCC314]

β-Noroxymorphol

Scheme 6

Surprisingly, additional hydrogenation time caused more ABUK-impurity to be formed. Higher temperatures, on the other hand caused higher formation of β-noroxymorphol as already known in the state of the art. See table 1

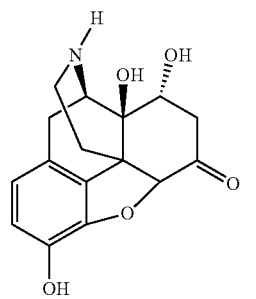

alpha-8-Hydroxynoroxymorphone
(α-8-OHN)

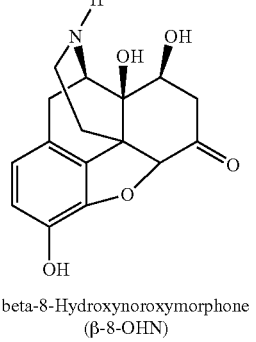

beta-8-Hydroxynoroxymorphone
(β-8-OHN)

Contrary, the state of the art shows that with strong acids used during hydrogenation it can be observed that the content of 8-OHN may be increased during hydrogenation.

The following table shows examples of pure 8-OHN in different acidic systems.

TABLE 1

| Example | Conditions | ABUK (HPLC-MS [ppm]) | 8-Hydroxy-noroxymor-phone [%] | Noroxy-morphol (HPLC a %) |
|---|---|---|---|---|
| 1 | T = 20° C., p = 5 bar, reaction time: 20 h. | 124 | 0.05 | 1.00 |
| 2 | T = 40° C., p = 10 bar, reaction time: 20 h. | 175 | 0.34 | 4.56 |
| 3 | T = 20° C., p = 5 bar, reaction time: 17 h | 144 | 0.28 | 1.36 |
| 4 | T = 20° C., p = 5 bar. reaction time: 24 h; | 166 | 0.28 | 2.06 |
| 5 | T = 60° C., p = 5 bar. reaction time: 5 h; | 124 | 0.58 | 6.26 |

In order to shift the equilibrium from the 8OHN-impurity towards ABUK-impurity several organic and/or inorganic acids were tested. Although some of these acids have been used in the state of the art, there is no prior art known where the equilibrium could be shifted towards the ABUK-impurity to a higher extend. This has been explained with the theory that from the two stereoisomers, namely the alpha- and the beta-hydroxynoroxymorphone (alpha-8OHN and beta 8OHN) only one is easily dehydrogenation, but the other is not.

TABLE 2

| Example | Conditions | ABUK [Area %] | 8-Hydroxynor-oxymorphone [Area %] |
|---|---|---|---|
| 6 | AcOH (50 wt %), HCl (6M), 100° C. | 55 | 45 |
| 7 | AcOH (50 wt %), Water, 85° C. | 1 | 99 |
| 8 | AcOH (50 wt %), Water, 35° C., Sulfuric acid, 15 wt % | 35 | 65 |
| 9 | AcOH (50 wt %), Water, 50° C., Sulfuric acid 10 wt % | 49 | 51 |
| 10 | AcOH (50 wt %), Water, 75° C., Sulfuric acid, 10 wt % | 77 | 23 |
| 11 | Water, sulfuric Acid, 15 wt. %?+0 9000 | 88 | 12 |
| 12 | Water, sulfuric Acid, 15 wt. %, 8000 | 86 | 14 |
| 13 | Water, AcOH 50 wt %, sulfuric Acid, 15 wt. %, 80° C. | 65 | 35 |
| 14 | Water, AcOH, phosphoric acid, 37 wt. %, 80° C. | 12 | 88 |
| 15 | Water, phosphoric acid, 70 wt. %, 90° C. | 20 | 80 |

As can be seen in table 2, it is advantageous to use sulfuric acid in order to shift the equilibrium towards the ABUK-impurity. Also, high temperatures are important for the formation of ABUK. High temperatures only, using other acids or the use of sulfuric acid alone does not solve the problem of shifting the equilibrium towards the ABUK-impurity. According to the results in the equilibrium of the two impurities, the hydrogenation procedure was adjusted. This was to prove that in contrast to the state of the art a strong acid in hydrogenation reaction could not only help to reduce the amount of ABUK, but also the amount of 8-OHN.

Although high temperatures have been reported as not advantageous for the impurity profile of the product (see formation of noroxymorphol in Examples 1-5 and Examples in WO2015015147), it was decided to try high temperatures in combination with sulfuric acid.

The medium containing sulfuric acid was used in order to increase the content of the ABUK-impurity in the reaction solution. The temperature was furthermore raised to 80° C. or higher, since this temperature was beneficial for the formation of ABUK-impurity. Surprisingly, an increase of the noroxymorphol-impurity was not observed, although according to the teaching of WO2015015147 an increase of the noroxymorphol-impurity level was expected. According to the teaching of WO2015015147 noroxymorphol is formed when the temperature of the hydrogenation is raised to temperatures above 30° C.

TABLE 3

| Example | Conditions | ABUK [ppm] | 8-Hydroxynor-oxymorphone [ppm] | Noroxy-morphol (HPLC a %) |
|---|---|---|---|---|
| 16 | $H_2SO_4$(15.4 wt %), 6 bar, 70° C. | 120 | 718 | 0.14 |
| 17 | $H_2SO_4$(15.4 wt %), 6 bar, 80° C. | 74 | n.d. | 0.20 |
| 18 | $H_2SO_4$(15.4 wt %), 2 bar, 100° C. | 47 | n.d. | 0.17 |
| 19 | $H_2SO_4$(15.4 wt %), 6 bar, 100° C. | 34 | n.d. | 0.21 |
| 20 | $H_2SO_4$(10.2 wt %), 2 bar, 100° C. | 44 | 134 | 0.17 |
| 21 | $H_2SO_4$(10.2 wt %), 6 bar, 100° C. | 58 | 143 | 0.32 |
| 22 | $H_2SO_4$(15.4 wt %), 4 bar, 100° C. | 42 | n.d. | 0.25 |
| 23 | $H_2SO_4$(15.4 wt %), 4 bar, 115° C. | 18 | n.d. | 0.15 |
| 24 | $H_2SO_4$(17.2 wt %), 4 bar, 115° C. | 12 | n.d. | 0.12 | n.d. = not detected.
LOD = 0.01%

Table 3 shows that a concentration of at least 10.2 wt % of sulfuric acid in combination with a temperature of at least 80° C. shows significant improvement in the reduction of both impurities. Due to the limit of ABUK-impurities of 75 ppm for pharmaceutical compositions, the most important criterion is the content of the ABUK-impurity. The level of this impurity has to be below 75 ppm. Impurity levels of 8-OHN of less than 300 ppm where defined as acceptable.

We have thus found a way of converting the 8OHN-Impurity to ABUK and to subsequently hydrogenation ABUK to noroxymorphone in one step without isolating the intermediate.

It needs also to be addressed that with the procedure of the invention it is not necessary to perform the hydrogenation in two steps. WO2015015147 describes the advantages of a two-step hydrogenation. However, we have observed that this two-step procedure is not necessary if the teaching of this invention is employed.

For the invention it is important that the reaction is carried out in an acidic aqueous solution containing sulfuric acid in combination with a temperature of at least 80° C. Better results are achieved with temperatures of 100° C. or more or even temperatures of more than 110° C. Best results are achieved at reaction temperatures of 115° C. or more. In comparison, table 4 shows the results with phosphoric acid. A high hydrogenation temperature may reduce the ABUK-content, but it does not significantly reduce the content of 8-hydroxynoroxymorphone after workup. This example shows that only the combination of sulfuric acid with a temperature of at least 80° C. shows a significant reduction of the 8-hydroxynoroxymorphone in the mixture to a level of not more than 300 ppm.

TABLE 4

(comparative example)

| Example | Conditions | ABUK [ppm] | 8-Hydroxynor-oxymorphone [ppm] |
|---|---|---|---|
| 25 | $H_3PO_4$( 17 wt %), 5 bar, 80° C., 18 h | 21 | 1202 |

For the invention it is not important, what kind of catalyst is used in the hydrogenation. The hydrogenation catalyst may be selected as stated in the prior art. It may be "a heterogeneous or homogeneous catalyst, preferably a heterogeneous catalyst. The catalyst (whether heterogeneous or homogeneous) should be selected such that the catalyst preferentially enhances reduction of the double bond at C-7 and C-8 rather than reducing the C=O bond at C-6. In one embodiment, the heterogeneous catalyst is a heterogeneous platinum group metal (PGM) catalyst, for example, a heterogeneous palladium or platinum catalyst.

In one embodiment, the heterogeneous catalyst is a heterogeneous palladium catalyst. Examples of palladium catalysts include but are not limited to colloidal palladium, palladium sponge, palladium plate or palladium wire.

The heterogeneous PGM catalyst may be a PGM on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$Al_2O_3$, beta-$Al_2O_3$, gamma-$Al_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). An example of a heterogeneous PGM catalyst is palladium on carbon. An example of another heterogeneous PGM catalyst is platinum on carbon.

The catalyst loading may be up to about 20 mole %. In one embodiment, the catalyst loading may be up to 10 mole % and, in another embodiment, may be in the range of about 0.001-10 mole %, for example, 0.01-10 mole %. In another embodiment, the catalyst loading may be in the range of about 0.1-10.0 mole %." (see WO2015015147) Compounds named in this document include, if not otherwise defined also the corresponding pharmaceutically acceptable salt.

Stress Testing

The ABUK-regrowth tendency was tested under so called stress-conditions. These conditions are mimicking long lifetime of a solution and are performed in extreme pH-conditions.

The comparative example is taken from prior art document and has not been repeated in our laboratory.

TABLE 5

| Starting Material | Stress conditions | Before stress | | After Stress | |
|---|---|---|---|---|---|
| | | ABUK [ppm] | 8OHN [ppm] | ABUK [ppm] | 8OHN [ppm] |
| 16 | NaOH, pH 12, 80° C., 18h | 120 | 718 | 334 | 520 |
| 21 | | 58 | 143 | 174 | n.d. |
| 24 | | 12 | n.d. | 20 | n.d. |
| WO2015015147* | Basic, 80° C. over night | n.d. | n.a. | ~100 | n.a. | n.d. = not detected, n.a. = not analysed,
*comparative example from prior art

Definitions

ABUK describes all kinds of alpha-beta unsaturated compounds, especially compounds with a double bond at the C7-C8 of the morphinan structure.

8OHN describes if not otherwise defined 8-hydroxy-noroxymorphone in the alpha and beta form. It may also stand for other 8-Hydroxy derivatives with or without substituents at the nitrogen and the C3-Oxygen.

Reduction of impurities through a process means that the content of the respective impurity is less than before performing the process.

ppm describes the content of an impurity in parts per million. 1000 ppm corresponds to 0.1%.

Although, we have only shown the process of reducing ABUK-impurity and 8OHN-impurity in noroxymorphone containing solutions, there seems no obvious reason why this should not also work for other substrates like oxymorphone or oxycodone. Because the substituents at nitrogen or oxygen at C3 do not have any influence to the existence of an equilibrium of an alpha-beta unsaturated carbonyle (ABUK) and its water addition product, there are no well-founded reasons for believing that the skilled person would be unable, on the basis of the information given in the application, to extend the particular teaching of the description to other substrates by using routine methods of experimentation or analysis. The corresponding impurities may also be removed from the respective solutions by hydrogenation under the conditions of the current invention. It should therefore be allowed to cover all obvious equivalents to and uses of this invention in the claims.

We therefore also claim the reduction of the corresponding impurities in the following substrates:

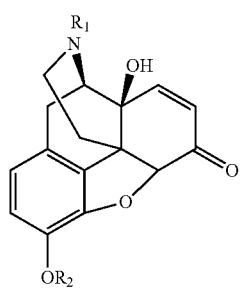

(I)

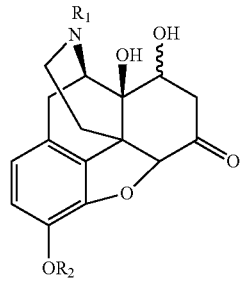

(II)

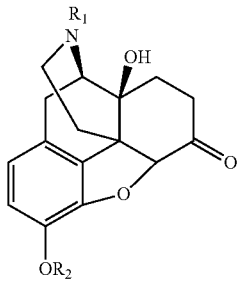

(III)

Wherein $R_1$ and $R_2$ are independently —H or —$CH_3$

Wherein in the preferred embodiments, $R_1$ and $R_2$ are H.

DETAILED DESCRIPTION OF THE INVENTION

The aim of the invention is to reduce both the content of compound (II) and compound (I) in a mixture with compound (III) to a level that reduces regrowth of compound (I)

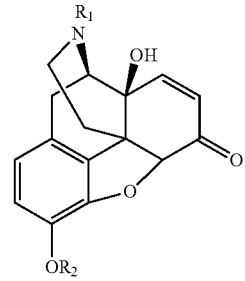

(I)

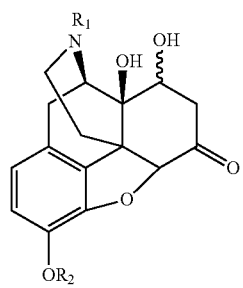

(II)

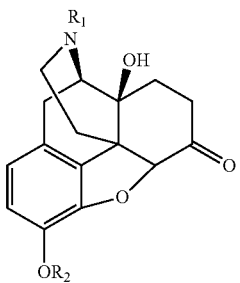
(III)

Wherein R₁ and R₂ are independently —H or —CH₃
Wherein in the preferred embodiments, R₁ and R₂ are H.

In one embodiment the invention is directed to a process for reducing the amount of compound of formula (I) and compound of formula (II) in a mixture of compound (I), compound (II) and compound (III), or solvates or salts thereof wherein the level of compound (I) is reduced to less than 75 ppm and wherein the level of compound (II) is reduced to less than 300 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 75 ppm and wherein the level of compound (II) is reduced to less than 200 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 75 ppm and wherein the level of compound (II) is reduced to less than 100 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 50 ppm and wherein the level of compound (II) is reduced to less than 300 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 50 ppm and wherein the level of compound (II) is reduced to less than 200 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 50 ppm and wherein the level of compound (II) is reduced to less than 100 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 25 ppm and wherein the level of compound (II) is reduced to less than 300 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 25 ppm and wherein the level of compound (II) is reduced to less than 200 ppm.

In another embodiment the invention is directed to a process for reducing the amount of compound of formula (I) and compound of formula (II) in a mixture of compound (I), compound (II) and compound (III), or solvates or salts thereof wherein the level of compound (I) is reduced to less than 25 ppm and wherein the level of compound (II) is reduced to less than 100 ppm.

For the process to achieve the task of the above mentioned embodiments it is important to have two parameters combined:
a) The presence of sulfuric acid and
b) A temperature of 80° C. or more By combining these parameters for the hydrogenation, the process may be done within one step. That is, no two hydrogenation steps at different temperatures are needed. Furthermore, the hydrogenation according to this invention reduces the content of compound (I) and compound (II) more effectively than processes known in the art.

The higher the temperature, the better the task is achieved.

Therefore in one embodiment the process for reducing the amount of compound of formula (I) and compound of formula (II) in a mixture of compound (I), compound (II) and compound (III) comprises hydrogenation of the mixture in a composition containing sulfuric acid (H₂SO₄) at a temperature of 80° C. or more.

In one embodiment, the process for reducing the amount of compound of formula (I) and compound of formula (II) in a mixture of compound (I), compound (II) and compound (III) comprises hydrogenation of the mixture in a composition containing sulfuric acid (H₂SO₄) at a temperature of 90° C. or more.

In one embodiment, the process for reducing the amount of compound of formula (I) and compound of formula (II) in a mixture of compound (I), compound (II) and compound (III) comprises hydrogenation of the mixture in a composition containing sulfuric acid (H₂SO₄) at a temperature of 100° C. or more.

In one embodiment, the process for reducing the amount of compound of formula (I) and compound of formula (II) in a mixture of compound (I), compound (II) and compound (III) comprises hydrogenation of the mixture in a composition containing sulfuric acid (H₂SO₄) at a temperature of more than 110° C.

In one embodiment, the process for reducing the amount of compound of formula (I) and compound of formula (II) in a mixture of compound (I), compound (II) and compound (III) comprises hydrogenation of the mixture in a composition containing sulfuric acid (H₂SO₄) at a temperature of 115° C. or more.

The higher the concentration of the sulfuric acid (H₂SO₄), the better the result. Therefore, in one embodiment, the process for reducing the amount of compound of formula (I) and compound of formula (II) in a mixture of compound (I), compound (II) and compound (III) comprises hydrogenation of the mixture in a composition containing sulfuric acid wherein the concentration of sulfuric acid is 10.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid wherein the concentration of sulfuric acid is 15.4 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid wherein the concentration of sulfuric acid is 17.2 wt % or more.

For best results, the concentration of the sulfuric acid is controlled additionally to the temperature therefore, In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 80° C. or more wherein the concentration of sulfuric acid is 10.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 80° C. or more wherein the concentration of sulfuric acid is 15.4 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 80° C. or more wherein the concentration of sulfuric acid is 17.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 90° C. or more wherein the concentration of sulfuric acid is 10.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 90° C. or more wherein the concentration of sulfuric acid is 15.4 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 90° C. or more wherein the concentration of sulfuric acid is 17.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 100° C. or more wherein the concentration of sulfuric acid is 10.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 100° C. or more wherein the concentration of sulfuric acid is 15.4 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 100° C. or more wherein the concentration of sulfuric acid is 17.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of more than 110° C. wherein the concentration of sulfuric acid is 10.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of more than 110° C. wherein the concentration of sulfuric acid is 15.4 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of more than 110° C. wherein the concentration of sulfuric acid is 17.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 115° C. or more wherein the concentration of sulfuric acid is 10.2 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 115° C. or more wherein the concentration of sulfuric acid is 15.4 wt % or more.

In one embodiment, the process for reducing the amount of compound of formula (I) and compound of formula (II) in a mixture of compound (I), compound (II) and compound (III) comprises hydrogenation of the mixture in a composition containing sulfuric acid ($H_2SO_4$) at a temperature of 115° C. or more wherein the concentration of sulfuric acid is 17.2 wt % or more.

EXAMPLES

Method for the Determination of Impurities in Noroxymorphone

Reagents 13 00 14 Acetonitrile for HPLC
10 85 00 Water Ph. Eur./USP
59 20 72 HCl 1 mol/l
59 61 43 Tris(hydroxymethyl)aminomethane, Sigma, 252859, MKBX5076V (ACS Reagent≥99.8%)
59 33 43 phosphoric acid p.a. for HPLC 85-90%

Standards

SD0175 7,8-Didehydronoroxymorphone
SD0428 Noroxycodone
SD0642 noroxymorphone
SD1376 Norcarbamate
SD1479 Norhydromorphon SD1480 Noroxymorphol HCl
SD1481 Nordihydromorphin HCl
SD1482 8-Hydroxynoroxymorphon Equipment Waters Alliance LC-System/Agilent 1200 series
Detector 2487/2489, VWD, DAD Agilent 1200 series
Vakuum Degasser
Analytik weight;

Preparation of Solutions

Peak Identity/SST-Stock Solution:

Ca. 2 mg 7.8-Didehydronoroxymorphon, Norhydromorphon, Noroxymorphol HCl, Nordihydromorphin HCl, 8-Hydroxynoroxymorphon are weight into a 10.0 ml volumetric flask and diluent filled up to 10.0 ml.

Peak Identity/SST-Solution:

18-22 mg noroxymorphone are weighed into a 20.0 ml volumetric flask and dissolved with ca. 10 ml diluent. Then, 1.5 ml 7.8-Didehydronoroxymorphon, 0.2 ml Norhydromorphone and 0.75 ml of each Noroxymorphol HCl, Nordihydromorphine HCl and 8-Hydroxynoroxymorphon are added and the flask filled up to the mark.

(Corresponds to: 3% 7.8-Didehydronoroxymorphon, 0.4% Norhydromorphon and 1.5% each of Noroxymorphol HCl, Nordihydromorphin HCl, 8-Hydroxynoroxymorphon for c=1.0 mg/ml)

Test Solution:

18-22 mg (accurately weighed) are dissolved and filled up to 20.0 ml Diluent. c=1.0 mg/ml.

Column: Waters
Type: Atlantis T3, 4.6×150 mm, 3.0 μm
Temperature oven: 25° C.+2° C.
Temperature autosampler: 5° C.+2° C.
Wavelength: 230 nm
Sampling rate: 5 pt/sec
Scale: y-Start: −0.02 y-End: 0.10

| Gradient | | | | |
|---|---|---|---|---|
| Time (min) | Flow (ml/min) | Eluent A (%) | Eluent B (%) | Curve Type |
| Initial | 0.6 | 100 | 0 | 6 |
| 10.0 | 0.6 | 100 | 0 | 6 |
| 15.0 | 1.2 | 95 | 5 | 6 |
| 18.0 | 1.2 | 95 | 5 | 6 |
| 23.0 | 1.2 | 50 | 50 | 6 |
| 25.0 | 1.2 | 5 | 95 | 6 |
| 27.0 | 1.2 | 5 | 95 | 6 |
| 28.0 | 0.6 | 100 | 0 | 6 |
| 33.0 | 0.6 | 100 | 0 | 6 |

Eluent A: 20 mM TRIS-Puffer pH 8.2
2.27 g TRIS in 940 ml distilled water Ph. Eur./USP, add 8.0 ml 1.0 mol/l
1M HCL and 60 ml Acetonitril. Mix
Eluent B: Acetonitril
Diluent: 0.85% Phosphoric acid
8.5 ml Phosphoric acid 85-90% and 1000 ml water.

| Sample | Function | Vial No. | No. | Inj. Vol. | Runtime |
|---|---|---|---|---|---|
| — | Purge Inj. | — | — | — | 10 min |
| — | Condition Column | — | — | — | 33 min |
| Blank | Inject Sample | 1 | 2 | 15 | 33 min |
| SST-solution | Inject Sample | 2 | 1 | 15 | 33 min |
| UM 1 | Inject Sample | 3 | 1 | 15 | 33 min |
| UM x | Inject Sample | 4 | 1 | 15 | 33 min |
| SST-solution | Inject Sample | 2 | 1 | 15 | 33 min |
| Blank | Inject Sample | 1 | 1 | 15 | 33 min |

| Substance | RT | RRT |
|---|---|---|
| 7,8-Didehydronoroxymorphone | 15.9 | 1.31 |
| Noroxycodone | 22.1 | 1.81 |
| Noroxymorphone | 12.2 | 1.00 |
| Norcarbamate | 24.0 | 1.98 |
| Norhydromorphone | 16.4 | 1.35 |
| Noroxymorphol HCl | 7.3 | 0.60 |
| Nordihydromorphine HCl | 8.9 | 0.74 |
| 8-Hydroxynoroxymorphon | 7.9 | 0.65 |
| Oxymorphon | 23.0 | 1.89 |

SST

Resolution (USP) between noroxymorphole HCl and 8-Hydroxynoroxymorphon 1.2

Resolution (USP) 8-Hydroxynoroxymorphon and nordihydromorphin HCl 1.5

Resolution (USP) between 7.8-Didehydronoroxymorphon and norhydromorphon 1.5

Calculation
  Area-%

Figure 2:
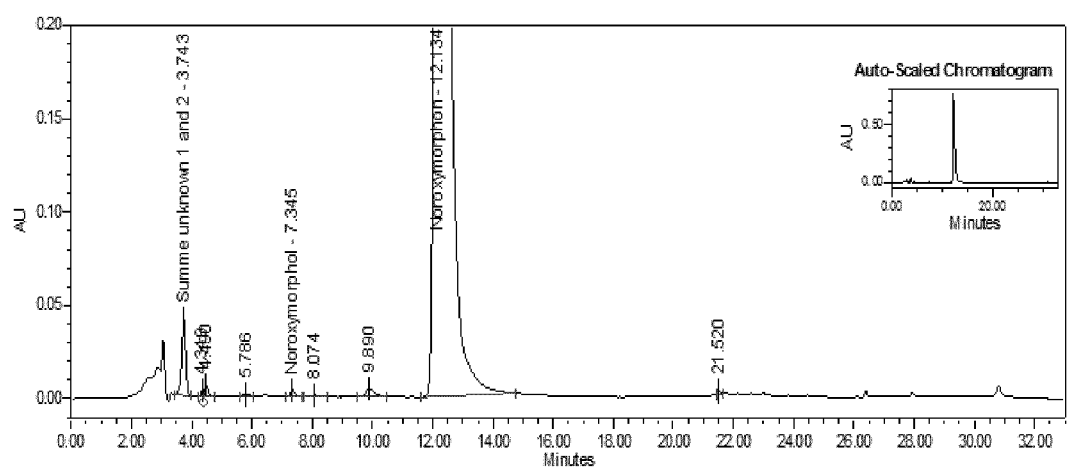
Figure 3:
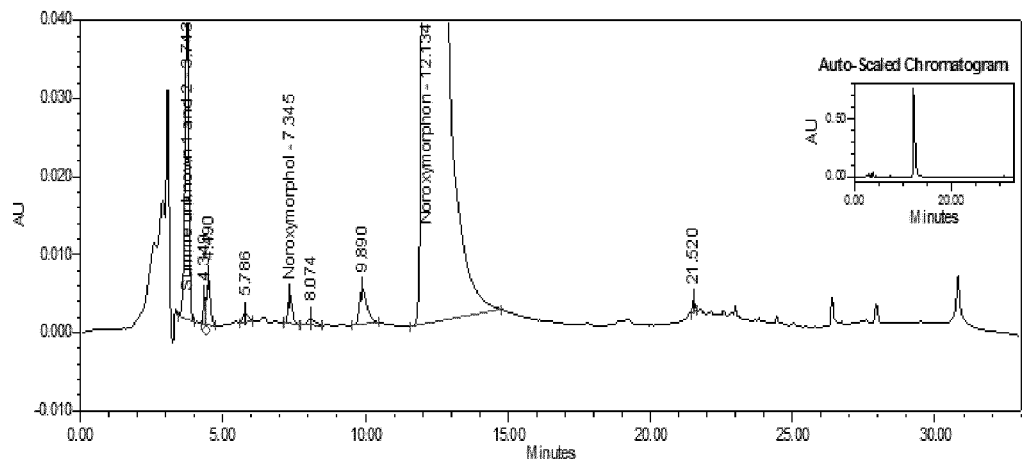
Figure 4:
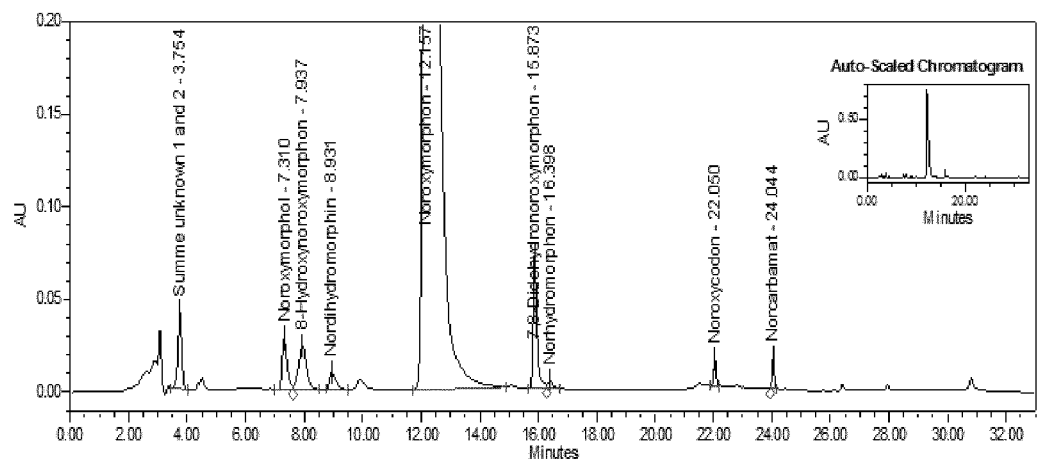

Sample Chromatograms
  (See Annex, FIGS. 1-4)

Method for the Determination of 7,8-Didehydronoroxymorphone

Chemicals
  Water MilliQ quality
  Acetonitrile LC-MS quality
  Ammonium acetate HPLC quality
  Ammonia solution ACS reagent Standards
  7,8-Didehydronoroxymorphone SD0175, Lot No. 0732Q009, AS-P 14-0353
  Note: As per certificate of analysis no potency is assigned for this standard, therefore its potency is—as a worst case approach—assumed as 100%.

Sample
  Noroxymorphone DS Lot No. 1337F011, AS-P 13-0363

HPLC-MS System
  For validation experiments a Waters Alliance 2795 HPLC and Quattro Micro MS were used:
  Autosampler Waters Alliance 2795
  Quaternary LC pump Waters Alliance 2795
  Column thermostat Jetstream
  Dual wavelength absorbance detector Waters 2487
  Mass spectrometer Micromass Quattro Micro API (Waters)
  Source gas, cone gas Nitrogen
  Ion source ESI
  Software: MassLynx V4.1 (Waters)

Chromatographic Conditions
  HPLC column: Zic HILIC (250×4.6 mm, 5 μm, DiChrom GmbH)
  Column temperature: 30° C.
  Temperature in autosampler: 5±3° C.
  Eluent A: 10 mM ammonium acetate pH 7/acetonitrile (20/80, v/v)
  Eluent B: 10 mM ammonium acetate pH 7/acetonitrile (40/60, v/v)
  Flow rate: 0.9 ml/min Needle wash solution: Acetonitrile/water (1/1, v/v) Purge solvent:
  Eluent A
Detection: SIR at m/z=286.0 [M+H]+ of 7,8-Didehydro-noroxy-morphone
Injection volume: 20 μL
Run-time: 30 min
Diluent: Eluent B

TABLE 2

Gradient program

| Time [min] | Eluent A [%] | Eluent B [%] | Flow [ml/min] |
|---|---|---|---|
| 0 | 100 | 0 | 0.900 |
| 5 | 100 | 0 | 0.900 |
| 20 | 0 | 100 | 0.900 |
| 25 | 0 | 100 | 0.900 |
| 26 | 100 | 0 | 0.900 |
| 30 | 100 | 0 | 0.900 |

Mass Spectrometric Conditions

The mass spectrometric conditions were optimized for the HPLC-ESI-MS system used. The conditions need to be checked and optimized to achieve optimal sensitivity for the determination of the 7,8-Didehydronoroxymorphone (e.g. after new calibration). The following parameters were used:

| Polarity | ES+ | Cone Gas Flow | 50 |
|---|---|---|---|
| Capillary (kV) | 4.0 | Desolvation | 750 |
| Cone (V) | 30.0 | Entrance | 30 |
| Extractor (V) | 3.0 | Collision | 1 |
| RF Lens (V) | 0.2 | Exit Energy (V) | 30 |
| Source | 130 | Multiplier | 750 |

All Parameters are input-values.
Selected Ion Recording Parameters (7,8-Didehydronoroxymorphone):
  Mass (Da) 286.1
  Dwell time (s) 0.50
  Inter channel delay (s) 0.10
  Inter scan time (s) 0.10
  Repeats 3.0
Preparation of Solutions
General Solutions
10 mM Ammonium Acetate Buffer pH 7:
  0.77 g of ammonium acetate were diluted in 1 L water and set to pH 7.0 with ammonia solution. The solution was prepared fresh weekly.
  Eluent A: 200 ml of 10 mM ammonium acetate buffer pH 7 were mixed with 800 ml acetonitrile and sonicated for 15 min.
  Eluent B: 400 ml of 10 mM ammonium acetate buffer pH 7 were mixed with 600 ml acetonitrile and sonicated for 15 min.
  Purge Solvent: Eluent A
  Diluent: Eluent B
Impurity Standard Solutions
7,8-Didehydronoroxymorphone Stock Standard Solution 1 (c=1.0 mg/ml):
  20.00 mg 7,8-Didehydronoroxymorphone were weighed accurately into a 20 ml volumetric flask, 20 μL acetic acid were added, made up to volume with diluent and mixed.
7,8-Didehydronoroxymorphone Stock Standard Solution 2 (c=0.1 mg/ml):
  1 ml 7,8-Didehydronoroxymorphone Stock standard solution 1 (c=1.0 mg/ml) was pipetted into a 10 ml volumetric flask, made up to volume with diluent and mixed.
7,8-Didehydronoroxymorphone Standard Solution 1 (c=0.01 mg/ml; 0.5%):
  1 ml 7,8-Didehydronoroxymorphone Stock standard solution 2 (c=0.1 mg/ml) was pipetted into a 10 ml volumetric flask, made up to volume with diluent and mixed.
7,8-Didehydronoroxymorphone Standard Solution 2 (c=0.0002 mg/ml; 100 ppm):
  200 μL 7,8-Didehydronoroxymorphone standard solution 1 (c=0.01 mg/ml; 0.5%) were pipetted into a 10 ml volumetric flask, made up to volume with diluent and mixed.
7,8-Didehydronoroxymorphone Standard Solution 3 (c=0.00015 mg/ml; 75 ppm):
  150 μL 7,8-Didehydronoroxymorphone standard solution 1 (c=0.01 mg/ml; 0.5%) were pipetted into a 10 ml volumetric flask, made up to volume with diluent and mixed.
7,8-Didehydronoroxymorphone Standard Solution 4 (c=0.00012 mg/ml; 60 ppm):
  120 μL 7,8-Didehydronoroxymorphone standard solution 1 (c=0.01 mg/ml; 0.5%) were pipetted into a 10 ml volumetric flask, made up to volume with diluent and mixed.
7,8-Didehydronoroxymorphone Standard Solution 5 (c=0.00010 mg/ml; 50 ppm):
  100 μL 7,8-Didehydronoroxymorphone standard solution 1 (c=0.01 mg/ml; 0.5%) were pipetted into a 10 ml volumetric flask, made up to volume with diluent and mixed.
7,8-Didehydronoroxymorphone Standard Solution 6 (c=0.00007 mg/ml; 35 ppm, SST):
  70 μL 7,8-Didehydronoroxymorphone standard solution 1 (c=0.01 mg/ml; 0.5%) were pipetted into a 10 ml volumetric flask, made up to volume with diluent and mixed.
7,8-Didehydronoroxymorphone Standard Solution 7 (c=0.00004 mg/ml; 20 ppm):
  1 ml 7,8-Didehydronoroxymorphone standard solution 2 (c=0.0002 mg/ml; 100 ppm) were pipetted into a 5 ml volumetric flask, made up to volume with diluent and mixed.
7,8-Didehydronoroxymorphone Standard Solution 8 (c=0.00002 mg/ml; 10 ppm):
  500 μL 7,8-Didehydronoroxymorphone standard solution 2 (c=0.0002 mg/ml; 100 ppm) were pipetted into a 5 ml volumetric flask, made up to volume with diluent and mixed.
7,8-Didehydronoroxymorphone Standard Solution 9 (c=0.00001 mg/ml; 5 ppm):
  250 μL 7,8-Didehydronoroxymorphone standard solution 2 (c=0.0002 mg/ml; 100 ppm) were pipetted into a 5 ml volumetric flask, made up to volume with diluent and mixed.
Noroxymorphone Sample Solution
Noroxymorphone Sample Solution (c=2 mg/ml):
  20.00 mg noroxymorphone sample were weighed accurately into a 10 ml volumetric flask. 20 μL acetic acid and about 9 ml diluents were added, the mixture was sonicated for about 5 min, made up to volume with diluent and mixed.
Spiked Noroxymorphone Solutions
  Note: All ppm values were calculated according to the noroxymorphone content (c=2 mg/ml).
Noroxymorphone Sample Solution (c=2 mg/ml) Spiked with 100 ppm 7,8-Didehydronoroxy-Morphone:
  20.00 mg noroxymorphone sample were weighed accurately into a 10 ml volumetric flask, about 20 μL acetic acid, 200 μL 7,8-Didehydronoroxymorphone standard solution 1 (c=0.01 mg/ml; 0.5%) and about 9 ml diluent were added, the mixture was sonicated for about 5 min, made up to volume with diluent and mixed.
  This solution was prepared in triplicate.
Noroxymorphone Sample Solution (c=2 mg/ml) Spiked with 75 ppm 7,8-Didehydronoroxy-Morphone:
  20.00 mg noroxymorphone sample were weighed accurately into a 10 ml volumetric flask, about 20 μL acetic acid, 150 µL 7,8-Didehydronoroxymorphone standard solution 1 (c=0.01 mg/ml; 0.5%) and about 9 ml diluent were added, the mixture was sonicated for about 5 min, made up to volume with diluent and mixed.

This solution was prepared in triplicate.

Noroxymorphone Sample Solution (c=2 mg/ml) Spiked with 35 ppm 7,8-Didehydronoroxy-Morphone:

20.00 mg noroxymorphone sample were weighed accurately into a 10 ml volumetric flask, about 20 µL acetic acid, 70 µL 7,8-Didehydronoroxymorphone standard solution 1 (c=0.01 mg/ml; 0.5%) and about 9 ml diluent were added, the mixture was sonicated for about 5 min, made up to volume with diluent and mixed.

This solution was prepared in triplicate.

Noroxymorphone Sample Solution (c=2 mg/ml) Spiked with 10 ppm 7,8-Didehydronoroxy-Morphone:

20.00 mg noroxymorphone sample were weighed accurately into a 10 ml volumetric flask, about 20 µL acetic acid, 1 ml 7,8-Didehydronoroxymorphone standard solution 2 (c=0.0002 mg/ml; 100 ppm) and about 8 ml diluent were added, the mixture was sonicated for about 5 min, made up to volume with diluent and mixed.

This solution was prepared in triplicate.

Analysis Sequence, SST and Calculation of Results

Column Maintenance and Equilibration

The HPLC system was equilibrated with the Eluent for one hour before analyzing samples.

The column was stored after use in acetonitrile/water 80/20, v/v.

System Suitability

The system suitability solution [7,8-Didehydronoroxymorphone standard solution 6 (35 ppm)] was injected five times in bracketing mode with relative standard deviation (RSD) of ≤20%.

For calculation of relative standard deviation (RSD), the first SST injection was neglected, because experiments showed, that this injection was needed for system equilibration. According to this a RSD 20% was fulfilled for all sequences analyzed during validation.

Calculation of Results The concentrations were calculated according to a mean standard 35 ppm derived from System Suitability. For determination of the mean peak area, the first SST injection was neglected, because experiments showed, that this injection was needed for system equilibration.

$$C_{sample} [ppm] = area_{sample} * 35 \text{ ppm/mean area}_{SST}$$

The Recovery rates (accuracy analyses) were determined as follows:

$$\text{Recovery } [\%] = 100 * \text{concentration}_{calculated} / \text{concentration}_{assumed}$$

Analysis Sequence, SST and Calculation of Results for Routine Analysis

Column Maintenance and Equilibration

The HPLC system was equilibrated with the eluent for one hour before analyzing samples. The column was stored after use in acetonitrile/water 80/20, v/v.

Analysis Sequence

For routine analysis the following sequence will be used:
1) Blank (Diluent)
2) Standard solution 35 ppm for equilibration
2) 7,8-Didehydronoroxymorphone Standard 35 ppm
3) 7,8-Didehydronoroxymorphone Standard 35 ppm
4) 7,8-Didehydronoroxymorphone Standard 35 ppm
5) 7,8-Didehydronoroxymorphone Standard 35 ppm
6) Spiked sample solution 35 ppm (non-spiked sample must be part of the sequence)
7) Blank (Diluent)
8) Sample injections[a]
9) 7,8-Didehydronoroxymorphone standard solution 6 (35 ppm)
10) 7,8-Didehydronoroxymorphone standard solution 6 (35 ppm)
11) Blank (Diluent)

[a] up to 5 samples in double preparation

System Suitability

The system suitability solution [7,8-Didehydronoroxymorphone standard solution 6 (35 ppm)] will be injected five times in bracketing mode with relative standard deviation (RSD) of ≤20%.

For calculation, the first injection of the standard solution (line 2: Standard solution 35 ppm for equilibration) will be neglected, because experiments showed, that this injection is needed for system equilibration.

Calculation of Results

The concentrations will be calculated according to a mean standard 35 ppm derived from system suitability. Furthermore, the matrix factor will be determined from the spiked sample solution and the non-spiked sample solution:

$$\text{Matrix factor } F = 35 \text{ ppm} / (area_{Spiked\ sample\ 35\ ppm} - area_{non-spiked\ sample})$$

$$C_{sample} [ppm] = F * area_{sample} * 35 \text{ ppm/mean area}_{SST}$$

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

If noroxymorphone crude or noroxymorphone containing ABUK and 8-OHN-impurity is used in the examples, the composition in the experiments contains at least 500 ppm ABUK impurity and/or at least 0.5% (=5000 ppm) 8-OHN-Impurity. The reactions may also be performed with higher or lower contents of these two impurities.

Example 1-5

Hydrogenation with more pressure and/or longer reaction time (comparative examples) 190.0 g noroxymorphone containing ABUK and 8-OHN-Impurity is charged to 1510 g water. 97.0 g acetic acid is added to the mixture. 10.0 g 5% Pd/C (E101 NN/W) is charged to the resulting solution. The suspension is hydrogenated at 20° C.-60° C. for at least 6 hours (up to 24 h) under 4-6 bar hydrogen. The hydrogenation is stopped, and the reactor is flushed with nitrogen. The reaction mixture is heated to 50° C. and filtered through a cellflock pad. The filter is washed with 109 g water and the filtrate is cooled to 20° C. and 574 g 2-propanol is added to the mixture. The resulting solution is treated with 30% aqueous sodium hydroxide to pH=9.0. The product precipitates. The suspension is stirred for 120 minutes at 20° C. and the solid is then isolated by centrifugation and washed with 72 g water, followed by 36 g acetone.

The wet product is unloaded and charged to a dryer. The wet material is dried at ≤100 mbar at 75° C. See table 1 for results.

Examples 6-15

Investigations Towards the Equilibrium of the Two Impurities 0.2 g 8-OHN was dissolved in 1.54 g water (7.7 parts in weight) and the required amount of acid to get the concentration as depicted in table 2. The clear solution was heated to the temperature as described in table 2, and checked for conversion after 24 h. The results are reported in the table 2.

Example 16

26.0 g noroxymorphone crude was suspended in 57.0 g deionized water, 11.0 g of 97% sulfuric acid were added, and the mixture was hydrogenated for 5 h on 1.0 g of 5% Pd/C under 6 bar hydrogen, at 70° C. After that time the temperature was reduced to 45° C. and the mixture was further hydrogenated under 6 bar hydrogen for additional 5 hours. The reaction mixture was decolored over charcoal, filtered and treated with 30% sodium hydroxide. The product precipitated and was isolated and dried at 85° C. (19.1 g noroxymorphone).

Example 17

26.0 g noroxymorphone crude was suspended in 57.0 g deionized water, 11.0 g of 97% sulfuric acid were added, and the mixture was hydrogenated for 5 h on 1.0 g of 5% Pd/C under 6 bar hydrogen, at 80° C. After that time the temperature was reduced to 20° C. and the pressure vessel was evacuated and flushed with nitrogen. The reaction mixture was decolored over charcoal, filtered and treated with 30% sodium hydroxide. The product precipitated and was isolated and dried at 85° C. (20.3 g noroxymorphone).

Example 18

26.0 g noroxymorphone crude was suspended in 57.0 g deionized water, 11.0 g of 97% sulfuric acid were added, and the mixture was hydrogenated for 5 h on 1.0 g of 5% Pd/C under 2 bar hydrogen, at 100° C. After that time the temperature was reduced to 20° C. and the pressure vessel was evacuated and flushed with nitrogen. The reaction mixture was decolored over charcoal, filtered and treated with 30% sodium hydroxide. The product precipitated and was isolated and dried at 85° C. (21.1 g noroxymorphone).

Example 19

26.0 g noroxymorphone crude was suspended in 57.0 g deionized water, 11.0 g of 97% sulfuric acid were added, and the mixture was hydrogenated for 5 h on 1.0 g of 5% Pd/C under 6 bar hydrogen, at 100° C. After that time the temperature was reduced to 20° C. and the pressure vessel was evacuated and flushed with nitrogen. The reaction mixture was decolored over charcoal, filtered and treated with 30% sodium hydroxide. The product precipitated and was isolated and dried at 85° C. (20.6 g noroxymorphone)

Example 20

26.0 g noroxymorphone crude was suspended in 91.0 g deionized water, 11.0 g of 97% sulfuric acid were added, and the mixture was hydrogenated for 5 h on 1.0 g of 5% Pd/C under 2 bar hydrogen, at 100° C. After that time the temperature was reduced to 20° C. and the pressure vessel was evacuated and flushed with nitrogen. The reaction mixture was decolored over charcoal, filtered and treated with 30% sodium hydroxide. The product precipitated and was isolated and dried at 85° C. (20.9 g noroxymorphone)

Example 21

26.0 g noroxymorphone crude was suspended in 91.0 g deionized water, 11.0 g of 97% sulfuric acid were added, and the mixture was hydrogenated for 5 h on 1.0 g of 5% Pd/C under 6 bar hydrogen, at 100° C. After that time the temperature was reduced to 45° C. and the mixture was further hydrogenated under 2 bar hydrogen for additional 5 hours. The reaction mixture was decolored over charcoal, filtered and treated with 30% sodium hydroxide. The product precipitated and was isolated and dried at 85° C. (21.3 g noroxymorphone)

Example 22

26.0 g noroxymorphone crude was suspended in 57.0 g deionized water, 11.0 g of 97% sulfuric acid were added, and the mixture was hydrogenated for 5 h on 1.0 g of 5% Pd/C under 4 bar hydrogen, at 100° C. After that time the temperature was reduced to 20° C. and the pressure vessel was evacuated and flushed with nitrogen. The reaction mixture was decolored over charcoal, filtered and treated with 30% sodium hydroxide. The product precipitated and was isolated and dried at 85° C. (21.5 g noroxymorphone)

Example 23

26.0 g noroxymorphone crude was suspended in 57.0 g deionized water, 11.0 g of 97% sulfuric acid were added, and the mixture was hydrogenated for 6 h on 1.0 g of 5% Pd/C under 4 bar hydrogen, at 115° C. After that time the temperature was reduced to 20° C. and the pressure vessel was evacuated and flushed with nitrogen. The reaction mixture was decolored over 2.0 g charcoal (Norit CAP Super) at 60° C., filtered (filter washed with 45 g deionized water at 50° C.) and treated with 30% sodium hydroxide at 55-65° C. The product precipitated and was isolated. The filter cake was washed with 60 g deionized water and 13 g acetone, and dried at 85° C. (21.1 g noroxymorphone).

Example 24

26.0 g noroxymorphone crude was suspended in 51.0 g deionized water, 11.0 g of 97% sulfuric acid were added, and the mixture was hydrogenated for 6 h on 1.0 g of 5% Pd/C under 4 bar hydrogen, at 115° C. After that time the temperature was reduced to 20° C. and the pressure vessel was evacuated and flushed with nitrogen.

The residue was decolored over 1.0 g charcoal (Norit CAP Super) at 50° C., filtered (filter washed with 23 g deionized water at 50° C.) and treated with 30% sodium hydroxide at 55-65° C. The product precipitated and was isolated. The filter cake was washed with 30 g deionized water and 7 g acetone, and dried at 85° C. (21 g noroxymorphone).

Example 25

Comparative Example from WO2016005923

To a 500-ml jacketed reactor was charged water (303 ml) and 85% aqueous $H_3PO_4$ (96.4 g, 2.4 molar equivalents). The solution was heated to about 50° C. with agitation and noroxymorphone (347.6 mmol, Batch 5) was added in several portions. The solution was heated to 75° C. and activated carbon (Darco KB-G, 30.0 g) was charged in one bolus.

The reaction mixture was heated to 90° C. and held at that temperature for about 4 hours. The hot reaction mixture was filtered through Whatman #1 filter paper and the carbon bed was rinsed with 260 ml of water to provide Filtrate 1 (795.1 g, about 715 ml). One portion of Filtrate 1 (401.9 g) was hydrogenated as follows. To a 300 ml pressure vessel was charged 199.4 g of Filtrate 1 (about 182 ml, about 25.0 g noroxymorphone) along with 2.5 g of 5% palladium on carbon (50% water wet, Johnson-Matthey).

To a separate 300 ml pressure vessel was charged 202.5 g of Filtrate 1 (about 183 ml, about 25.4 g noroxymorphone) along with 2.5 g of 5% palladium on carbon (50% water wet, Johnson-Matthey). Both reactors were purged and then heated to 80° C., pressurized with hydrogen to 517 kPa and stirred for 18 hours. The catalyst was filtered off and the remaining material was rinsed with water (2×20 ml/rinse). The combined filtrates were re-circulated through the catalyst bed once resulting in a transparent solution with no visible particulates. The two post hydrogenation filtrates were combined (401.9 g) and charged into a 4-neck 1-L round bottom flask. The pH of the solution was 2.0 at a temperature of about 25° C. The solution was stirred and heated to a temperature of 75° C. Ammonium hydroxide (28-30%, 84.7 g) was added dropwise over 45 minutes at 75° C. (pH 8.3). The mixture was cooled to 22° C. (pH 9.6). The solids were isolated by vacuum filtration and then the solids were washed with water (4×100 ml/wash). The wet cake was allowed to dry under suction for about 1 hour. The solids were dried at 80° C. under reduced pressure for about 18 hours. The dried solids (noroxymorphone, 48.7 g) were analyzed by HPLC

Example 26 Stress Testing

A sample of noroxymorphone (1 g) from different previous examples was dissolved in deionized Water (25 ml) and the pH was adjusted to pH 12 with 1 M NaOH. The solution was stirred in a water bath at 80° C. for 18 h and analysed.

The invention claimed is:

1. A process for reducing an amount of a compound of formula (I) and a compound of formula (II) in a mixture of the compound of formula (I), the compound of formula (II) and a compound of formula (III), or solvates or salts thereof

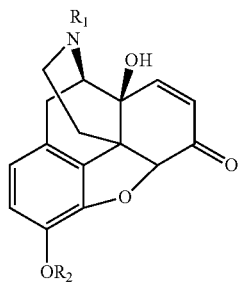

(I)

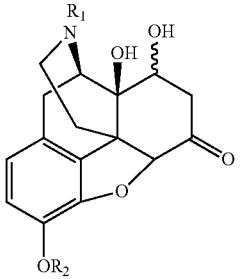

(II)

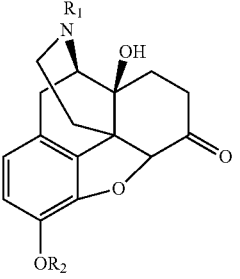

(III)

wherein $R_1$ and $R_2$ are independently hydrogen or $CH_3$, the process comprising:
hydrogenation of the mixture in a composition comprising sulfuric acid ($H_2SO_4$) at a temperature of 115° C. or more.

2. A process according to claim 1, wherein sulfuric acid is in a concentration of 10.2 wt % or more.

3. A process according to claim 1, wherein sulfuric acid is in a concentration of 15.4 wt % or more.

4. A process according to claim 1, wherein sulfuric acid is in a concentration of 17.2 wt % or more.

5. A process according to claim 1, wherein $R_1$ and $R_2$ are H.

* * * * *